United States Patent
Fan et al.

(10) Patent No.: US 11,931,403 B2
(45) Date of Patent: Mar. 19, 2024

(54) COMPOSITIONS, SYSTEMS, AND METHODS FOR TREATING OR REDUCING HYPOXIA-ISCHEMIA INDUCED BRAIN DAMAGE AND NEUROBEHAVIORAL DYSFUNCTION IN NEONATES

(71) Applicant: UNIVERSITY OF MISSISSIPPI MEDICAL CENTER, Jackson, MS (US)

(72) Inventors: Lir-Wan Fan, Brandon, MS (US); Abhay Jyotindrabhai Bhatt, Ridgeland, MS (US)

(73) Assignee: UNIVERSITY OF MISSISSIPPI MEDICAL CENTER, Jackson, MS (US)

( * ) Notice: Subject to any disclaimer, the term of this patent is extended or adjusted under 35 U.S.C. 154(b) by 730 days.

(21) Appl. No.: 16/891,789

(22) Filed: Jun. 3, 2020

(65) Prior Publication Data
US 2020/0376087 A1 Dec. 3, 2020

Related U.S. Application Data

(60) Provisional application No. 62/856,190, filed on Jun. 3, 2019.

(51) Int. Cl.

| | |
|---|---|
| *A61K 9/12* | (2006.01) |
| *A61K 9/00* | (2006.01) |
| *A61K 38/28* | (2006.01) |
| *A61M 31/00* | (2006.01) |
| *A61P 25/00* | (2006.01) |

(52) U.S. Cl.
CPC ............ *A61K 38/28* (2013.01); *A61K 9/0043* (2013.01); *A61M 31/00* (2013.01); *A61P 25/00* (2018.01); *A61M 2210/0618* (2013.01); *A61M 2210/0693* (2013.01); *A61M 2240/00* (2013.01)

(58) Field of Classification Search
CPC ......... A61M 15/08; A61M 11/00; A61K 9/12; A61K 9/124
See application file for complete search history.

(56) References Cited

PUBLICATIONS

Perlman (Intervention Strategies for Neonatal Hypoxia-Ischemic Cerebral Injury, Clinical Therapeutics, vol. 28, No. 9, 2006) (Year: 2006).*
Lin et al (Intranasal administration of IGF-1 attenuates hypoxic-ischemic brain injury in neonatal rats, Experimental Neurology, 217, 2009, 361-370) (Year: 2009).*
Duarte et al (Insulin neuroprotection against oxidation stress is mediated by Akt and GSK-3β signaling pathways and changes in protein expression, Biochimicet Biophysica Acta, Molecular Cell Research, vol. 1783, issue 6, 2008, p. 994-1002) (Year: 2008).*
Shah et al (Insulin delivery methods: Past, present and future, International Journal of Pharmaceutical Investigation, Jan. 2016, vol. 6, Issue 1) (Year: 2016).*
Benedict et al (Intranasal insulin improves memory in humans, Psychoneuroendocrinology, 2004, 29, 1326-1334 (Year: 2004).*
Shankaran S, Laptook AR, Ehrenkranz RA, et al. Whole-body hypothermia for neonates with hypoxic-ischemic encephalopathy. N Engl J Med 2005;353:1574-84.
Laptook AR, Shankaran S, Tyson JE, et al. Effect of Therapeutic Hypothermia Initiated After 6 Hours of Age on Death or Disability Among Newborns With Hypoxic-Ischemic Encephalopathy: A Randomized Clinical Trial. JAMA 2017;318:1550-60.
Shankaran S, Laptook AR, Pappas A, et al. Effect of Depth and Duration of Cooling on Death or Disability at Age 18 Months Among Neonates With Hypoxic-Ischemic Encephalopathy: A Randomized Clinical Trial. JAMA 2017;318:57-67.
Committee on F, Newborn, Papile LA, et al. Hypothermia and neonatal encephalopathy. Pediatrics 2014;133:1146-50.
Vannucci RC, Perlman JM. Interventions for perinatal hypoxic-ischemic encephalopathy. Pediatrics 1997;100:1004-14.
Hagberg H, David Edwards A, Groenendaal F. Perinatal brain damage: The term infant. Neurobiol Dis 2016;92:102-12.
Banks WA, Owen JB, Erickson MA. Insulin in the brain: there and back again. Pharmacol Ther 2012;136:82-93.
Sun X, Yao H, Douglas RM, Gu XQ, Wang J, Haddad GG. Insulin/PI3K signaling protects dentate neurons from oxygen-glucose deprivation in organotypic slice cultures. J Neurochem 2010;112:377-88.
Kim SJ, Han Y. Insulin inhibits AMPA-induced neuronal damage via stimulation of protein kinase B (Akt). J Neural Transm (Vienna) 2005;112:179-91.
Ribeiro M, Rosenstock TR, Oliveira AM, Oliveira CR, Rego AC. Insulin and IGF-1 improve mitochondrial function in a PI-3K/Akt-dependent manner and reduce mitochondrial generation of reactive oxygen species in Huntington's disease knock-in striatal cells. Free Radic Biol Med 2014;74:129-44.
Benedict C, Hallschmid M, Hatke A, et al. Intranasal insulin improves memory in humans. Psychoneuroendocrinology 2004;29:1326-34.
Reger MA, Watson GS, Frey WH, 2nd, et al. Effects of intranasal insulin on cognition in memory-impaired older adults: modulation by APOE genotype. Neurobiol Aging 2006;27:451-8.
Fernandez AM, Torres-Aleman I. The many faces of insulin-like peptide signalling in the brain. Nat Rev Neurosci 2012;13:225-39.
Crowe TP, Greenlee MHW, Kanthasamy AG, Hsu WH. Mechanism of intranasal drug delivery directly to the brain. Life Sci 2018;195:44-52.

(Continued)

*Primary Examiner* — Micah Paul Young
(74) *Attorney, Agent, or Firm* — Workman Nydegger

(57) ABSTRACT

A method for treating or reducing a likelihood of hypoxia-ischemia induced brain damage and neurobehavioral dysfunction in neonates utilizes a relative high dose of nasally administered insulin. In one aspect, the method includes intranasally administering, to a neonate in need thereof, an effective dose of insulin comprising between 350 U to 2000 U insulin.

20 Claims, 6 Drawing Sheets
(3 of 6 Drawing Sheet(s) Filed in Color)

(56) References Cited

PUBLICATIONS

Freiherr J, Hallschmid M, Frey WH, 2nd, et al. Intranasal insulin as a treatment for Alzheimer's disease: a review of basic research and clinical evidence. CNS Drugs 2013;27:505-14.

Rice JE, 3rd, Vannucci RC, Brierley JB. The influence of immaturity on hypoxic-ischemic brain damage in the rat. Ann Neurol 1981;9:131-41.

Patel SD, Pierce L, Ciardiello A, et al. Therapeutic hypothermia and hypoxia-ischemia in the term-equivalent neonatal rat: characterization of a translational preclinical model. Pediatr Res 2015;78:264-71.

Pang Y, Lin S, Wright C, et al. Intranasal insulin protects against substantia nigra dopaminergic neuronal loss and alleviates motor deficits induced by 6-OHDA in rats. Neuroscience 2016;318:157-65.

Fan LW, Lin S, Pang Y, et al. Hypoxia-ischemia induced neurological dysfunction and brain injury in the neonatal rat. Behav Brain Res 2005;165:80-90.

Fan LW, Lin S, Pang Y, Rhodes PG, Cai Z. Minocycline attenuates hypoxia-ischemia-induced neurological dysfunction and brain injury in the juvenile rat. Eur J Neurosci 2006;24:341-50.

Lan KM, Tien LT, Cai Z, et al. Erythropoietin Ameliorates Neonatal Hypoxia-Ischemia-Induced Neurobehavioral Deficits, Neuroinflammation, and Hippocampal Injury in the Juvenile Rat. Int J Mol Sci 2016;17:289.

Altman J, Sudarshan K. Postnatal development of locomotion in the laboratory rat. Anim Behav 1975;23:896-920.

Schmued LC, Stowers CC, Scallet AC, Xu L. Fluoro-Jade C results in ultra high resolution and contrast labeling of degenerating neurons. Brain Res 2005; 1035:24-31.

Vannucci RC, Brucklacher RM, Vannucci SJ. Glycolysis and perinatal hypoxic-ischemic brain damage. Dev Neurosci 2005;27:185-90.

Hefter D, Marti HH, Gass P, Inta D. Perinatal Hypoxia and Ischemia in Animal Models of Schizophrenia. Front Psychiatry 2018;9:106.

Feng Y, Lu S, Wang J, Kumar P, Zhang L, Bhatt AJ. Dexamethasone-induced neuroprotection in hypoxic-ischemic brain injury in newborn rats is partly mediated via Akt activation. Brain Res 2014;1589:68-77.

Kang S, Song J, Kang H, Kim S, Lee Y, Park D. Insulin can block apoptosis by decreasing oxidative stress via phosphatidylinositol 3-kinase- and extracellular signal-regulated protein kinase-dependent signaling pathways in HepG2 cells. Eur J Endocrinol 2003;148:147-55.

Fan LW, Carter K, Bhatt A, Pang Y. Rapid Transport of Insulin to the Brain Following Intranasal Administration in Rats. Neural Regeneration Research 2019;14.

Guo Z, Chen Y, Mao YF, et al. Long-term treatment with intranasal insulin ameliorates cognitive impairment, tau hyperphosphorylation, and microglial activation in a streptozotocin-induced Alzheimer's rat model. Sci Rep 2017;7:45971.

Marks DR, Tucker K, Cavallin MA, Mast TG, Fadool DA. Awake intranasal insulin delivery modifies protein complexes and alters memory, anxiety, and olfactory behaviors. J Neurosci 2009;29:6734-51.

Reger MA, Watson GS, Green PS, et al. Intranasal insulin administration dose-dependently modulates verbal memory and plasma amyloid-beta in memory-impaired older adults. J Alzheimers Dis 2008;13:323-31.

Lubics A, Reglodi D, Tamas A, et al. Neurological reflexes and early motor behavior in rats subjected to neonatal hypoxic-ischemic injury. Behav Brain Res 2005;157:157-65.

LeBlanc MH, Qian XB, Cai ZW. The effect of glucose during ischemia on brain ATP, lactate, and glutamate in piglets. Biol Neonate 1997;72:243-54.

Chang YS, Park WS, Ko SY, et al. Effects of fasting and insulin-induced hypoglycemia on brain cell membrane function and energy metabolism during hypoxia-ischemia in newborn piglets. Brain Res 1999;844:135-42.

Zhang X, Tang N, Hadden TJ, Rishi AK. Akt, FoxO and regulation of apoptosis. Biochim Biophys Acta 2011;1813:1978-86.

Jiang ZY, Zhou QL, Coleman KA, Chouinard M, Boese Q, Czech MP. Insulin signaling through Akt/protein kinase B analyzed by small interfering RNA-mediated gene silencing. Proc Natl Acad Sci U S A 2003;100:7569-74.

Zhou H, Li XM, Meinkoth J, Pittman RN. Akt regulates cell survival and apoptosis at a postmitochondrial level. J Cell Biol 2000;151:483-94.

* cited by examiner

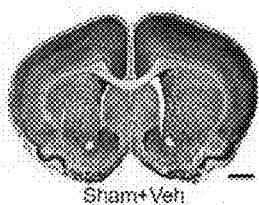 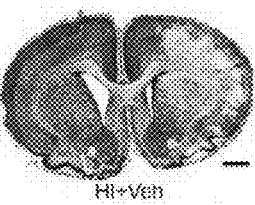 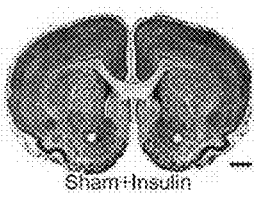 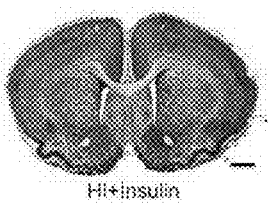
FIG. 4A     FIG. 4B     FIG. 4C     FIG. 4D
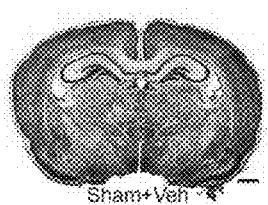 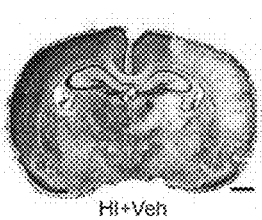 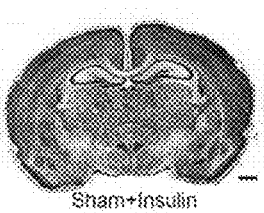 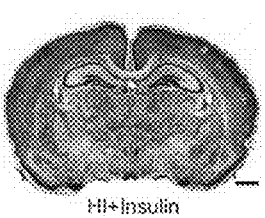
FIG. 4E     FIG. 4F     FIG. 4G     FIG. 4H
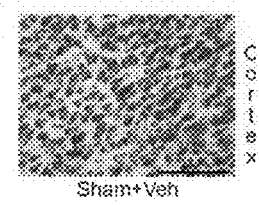 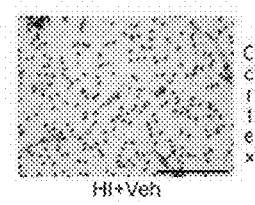 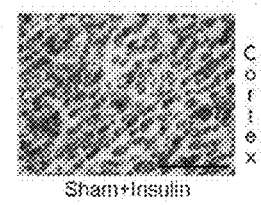 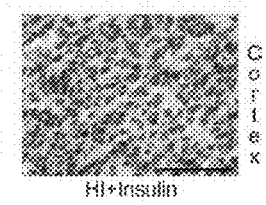
FIG. 4I     FIG. 4J     FIG. 4K     FIG. 4L
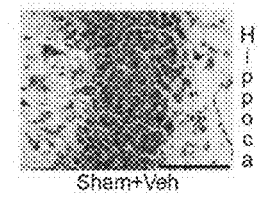 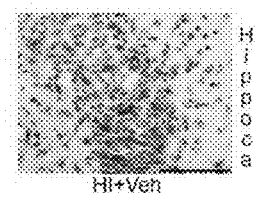 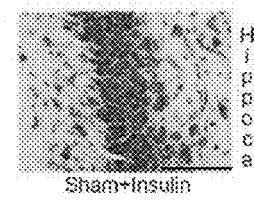 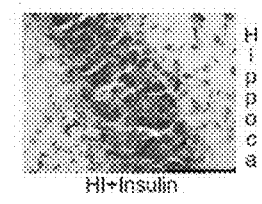
FIG. 4M     FIG. 4N     FIG. 4O     FIG. 4P
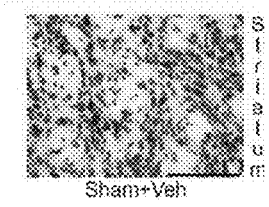 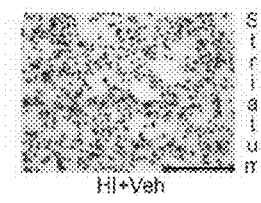 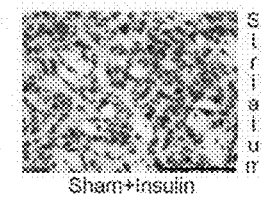 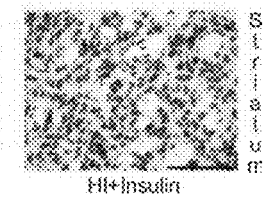
FIG. 4Q     FIG. 4R     FIG. 4S     FIG. 4T

COMPOSITIONS, SYSTEMS, AND METHODS FOR TREATING OR REDUCING HYPOXIA-ISCHEMIA INDUCED BRAIN DAMAGE AND NEUROBEHAVIORAL DYSFUNCTION IN NEONATES

CROSS-REFERENCE TO RELATED APPLICATIONS

This application claims priority to and the benefit of U.S. Provisional Patent Application Ser. No. 62/856,190, filed Jun. 3, 2019 and titled "REDUCTION OF HYPOXIA-ISCHEMIA INDUCED BRAIN DAMAGE AND NEUROBEHAVIORAL DYSFUNCTION IN NEONATES BY INTRANASAL INSULIN TREATMENT," which is incorporated herein by this reference in its entirety.

STATEMENT REGARDING FEDERALLY SPONSORED RESEARCH

The invention was made with government support under R01NS080844 awarded by the National Institutes of Health/National Institute of Neurological Disorders and Stroke. The government has certain rights in the invention.

BACKGROUND

Technical Field

This disclosure generally relates to treatment methods and the compositions and systems used in the same. More specifically, the present disclosure relates to methods for treating or reducing hypoxia-ischemia induced brain damage and neurobehavioral dysfunction in neonates and the compositions and systems used in the same.

Related Technology

Hypoxic ischemia (HI) occurs when there is insufficient oxygen resulting from reduced blood flow. Hypoxic-ischemic encephalopathy (HIE) is a type of brain dysfunction that occurs when the brain does not receive enough oxygen or blood flow for a period of time. In neonates, HIE may develop during pregnancy, labor, and/or delivery, or in the postnatal period. HIE can also occur in newborn infants with congenital heart disease or during cardiac arrest in the postnatal period in critically ill newborns. Typically, a newborn's body can compensate for brief periods of depleted oxygen, but if the asphyxia lasts too long, brain tissue is destroyed. Hypoxic-ischemic encephalopathy due to fetal or neonatal asphyxia is a leading cause of death or severe impairment among infants.

Some children will experience no health issues—or only mild or moderate effects—from HIE, while others have much more severe and permanent disability, such as developmental delay; cerebral palsy (motor impairment); epilepsy; or cognitive impairment.

If the blood or oxygen supply to the brain has been interrupted, the rest of the body may have also been "starved" of oxygen. This may cause damage to other organs, including the heart, liver, kidneys, and bowels. These organs usually return to normal function. However, if the brain has sustained an injury, it may not recover fully. The length of time the brain was without oxygen usually determines the severity of the damage.

Hypoxic-ischemic encephalopathy is most common in full-term infants, although it does occur in premature infants as well. The timing and severity of asphyxia can affect the area of the brain that sustains the injury. If injury occurs before week 35 in fetal development, HIE is likely to produce periventricular leukomalacia, or PVL. At 40 weeks, the degree of hypoxia correlates to the area of the brain that is injured; mild hypoxia usually affects the parasagittal white matter while severe hypoxia usually affects the putamen, thalamus, and paracentral white matter. The area of the brain that is affected often has a significant bearing on symptoms the child experiences.

Once HIE is suspected, neuroimaging techniques, especially MRIs, are performed to aid diagnosis. New techniques, including diffusion-weighted imaging and MR spectroscopy, are thought to be effective when used within the appropriate time frame. In order to perform these tests, doctors must first suspect HIE. If the birth was traumatic, or if a significant risk factor such as fetal stroke was known to occur during pregnancy, hypoxic-ischemic encephalopathy might be suspected at birth. Otherwise, parents, doctors, and caretakers take notice of visible signs—impaired motor function, delayed developmental milestones, and delayed growth through clinical observation over time. Certain signs may appear shortly after birth. Organ dysfunction, especially of the heart, lungs, kidneys, liver, and blood, indicates possible HIE. Seizures in the first 24 hours of life can also indicate the possibility of HIE.

Despite current advances in neonatal care and a newer therapy of moderate therapeutic hypothermia (TH), hypoxic ischemia (HI), particularly HIE, still causes significant morbidity and mortality in the neonatal period. Therapeutic hypothermia induced by cooling either the head or the whole body is the only treatment currently employed to reduce death and disability, and only in late preterm and term infants. Even so, initiation of TH beyond 6 hours of an HI insult (or suspected HI insult) is uncertain. Recent randomized control trials and review articles state the incidence of death and disability remains high (21-40%) even after treatment with cooling.

Clearly, current therapies have limited use and efficacy, and there is an urgent need for additional therapies to further improve outcomes of infants who have or are suspected to have acute HIE.

BRIEF SUMMARY

Implementations of the present disclosure solve one or more of the foregoing or other problems in the art with methods for treating or reducing hypoxia-ischemia induced brain damage and neurobehavioral dysfunction in neonates and the compositions and systems used in the same. In particular, one or more implementations can include a method for treating or reducing a likelihood of hypoxia-ischemia induced brain damage and neurobehavioral dysfunction in neonates by intranasally administering, to a neonate in need thereof, an effective high dose of intranasal insulin (InInsulin) comprising between 350 U to 2000 U insulin.

In one aspect, the effective dose of InInsulin is calculated at between 75 U to 700 U insulin per kilogram of the neonate. In such an embodiment, intranasally administering the effective dose of InInsulin includes intranasally delivering half of the effective dose to each nare of the neonate. In one aspect, the effective dose is from 1200 U to 1400 U insulin and is delivered intranasally at 600 U to 700 U insulin to each nare of the neonate.

In one aspect, the neonate is at least 36 weeks of gestational age at birth.

In one aspect, the treatment method further includes the act of identifying the neonate as having experienced, or who is suspected as having experienced, a hypoxic-ischemic event.

For any of the disclosed methods, the intranasal administration is provided to the neonate without causing systemic hypoglycemia. Intranasal administration can be provided to the neonate at one or more days between delivery and 28 days post-delivery of the neonate. In one implementation, the intranasal administration is provided to the neonate within 1 hour to 1 day after the experienced or suspected hypoxic-ischemic event. In one aspect, intranasal administration is provided to the neonate only one time.

In one aspect, the intranasal administration of InInsulin is provided to the neonate in the form of a nasal spray. The spray is provided as a high dose InInsulin suspension in aqueous saline solution or as a lyophilized powder to be suspended in aqueous saline solution. The high dose InInsulin suspension administered intranasally to the neonate is at least five times greater than the typical injection concentration, about 100 U/ml, for controlling diabetes. In such implementations, intranasal administration can include administering 25-150 μL of the nasal spray to each nare of the neonate. In an exemplary implementation, intranasal administration includes administering 50 μL of the nasal spray to each nare of the neonate at a concentration between 10,000 U/mL and 15,000 U/mL.

Additional and alternative methods of the present disclosure are also provided. For example, a method for treating or reducing a likelihood of hypoxia-ischemia induced brain damage and neurobehavioral dysfunction in neonates can include (i) identifying a neonate having experienced, or who is suspected as having experienced, a hypoxic-ischemic event; (ii) intranasally administering from 175 U to 1000 U, or 600 U to 700 U, InInsulin to each nare of the neonate without causing systemic hypoglycemia; and (iii) reducing a likelihood of hypoxia-ischemia induced brain damage and neurobehavioral dysfunction in the neonate.

In one aspect of the methods, the neonate is at least 36 weeks gestational age at birth.

In one aspect of the methods, intranasal administration includes administering 50 μL of a nasal spray to each nare of the neonate at a concentration of 14,000 U/mL.

Systems of the present disclosure can also include a system for treating or reducing a likelihood of hypoxia-ischemia induced brain damage and neurobehavioral dysfunction in neonates. In one aspect, the system includes (i) a single dose vial comprising between 350 U to 2000 U intranasal insulin suspended within an aqueous saline solution or as a powder to be suspended an aqueous saline solution and (ii) an intranasal delivery device operably connected to the single dose vial. The intranasal deliver device can be sized and shaped to prevent accidental administration of a by intradermal, subcutaneous, or intravenous routes of administration. In one aspect of the system, the intranasal delivery device is operable to deliver the single dose as two intranasal puffs, each intranasal puff comprising about 175 U to 1000 U intranasal insulin and being delivered to a different nare of the same neonate. Aspects of the system include the single dose vial having between 10,000 U/mL intranasal insulin suspended within 150 μL of the aqueous saline solution and 15,000 U/mL intranasal insulin suspended within 50 μL of the aqueous saline solution.

In one aspect of the disclosed systems, the single dose vial comprises between 10,000 U/mL to 15,000 U/mL intranasal insulin in a suspension of about 100 μL of the aqueous saline solution.

Accordingly, methods and systems for treating or reducing a likelihood of hypoxia-ischemia induced brain damage and neurobehavioral dysfunction in neonates after delivery are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

The patent or application file contains at least one drawing executed in color. Copies of this patent or application publication with color drawing(s) will be provided by the Office upon request and payment of the necessary fee.

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

Figure 1A:
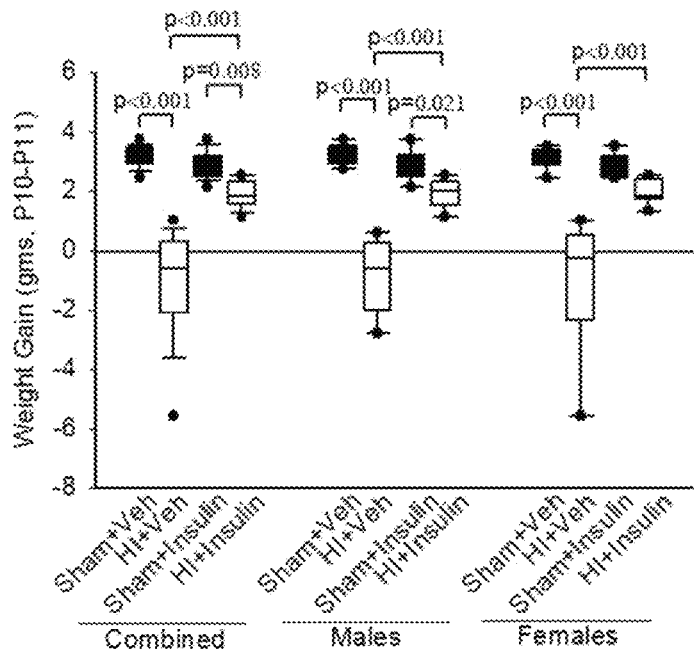

The disclosure will be described and explained with additional specificity and detail through the use of the accompanying drawings in which:

FIG. 1A illustrates a graph of body weight data from pups at day 11 post-delivery (P11) provided intranasal insulin (InInsulin) treatment following hypoxic-ischemic (HI) or Sham at day 10 post-delivery (P10).

Figure 1B:
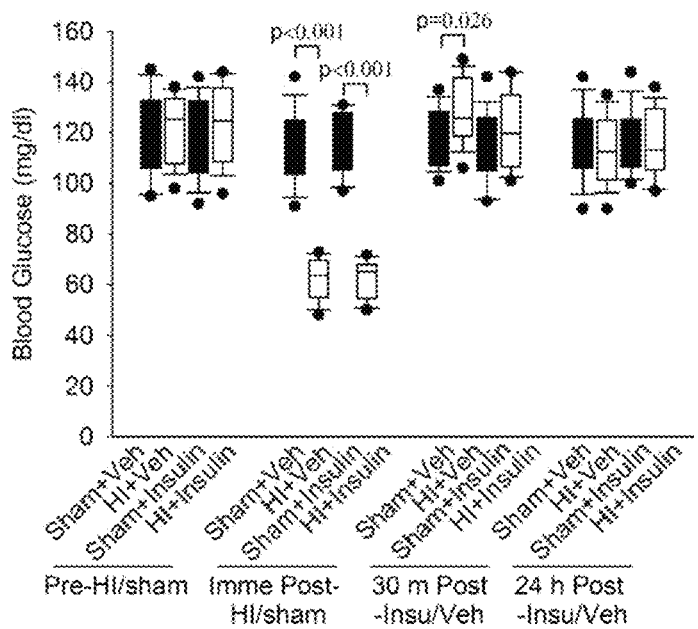
Figures 2A, 2B:
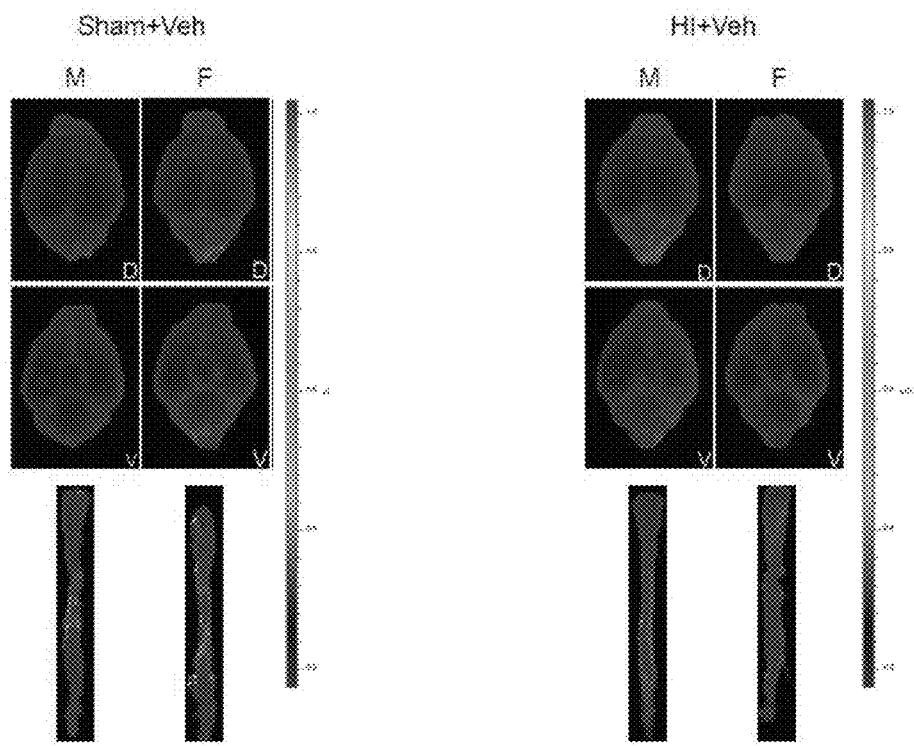
Figures 2C, 2D:
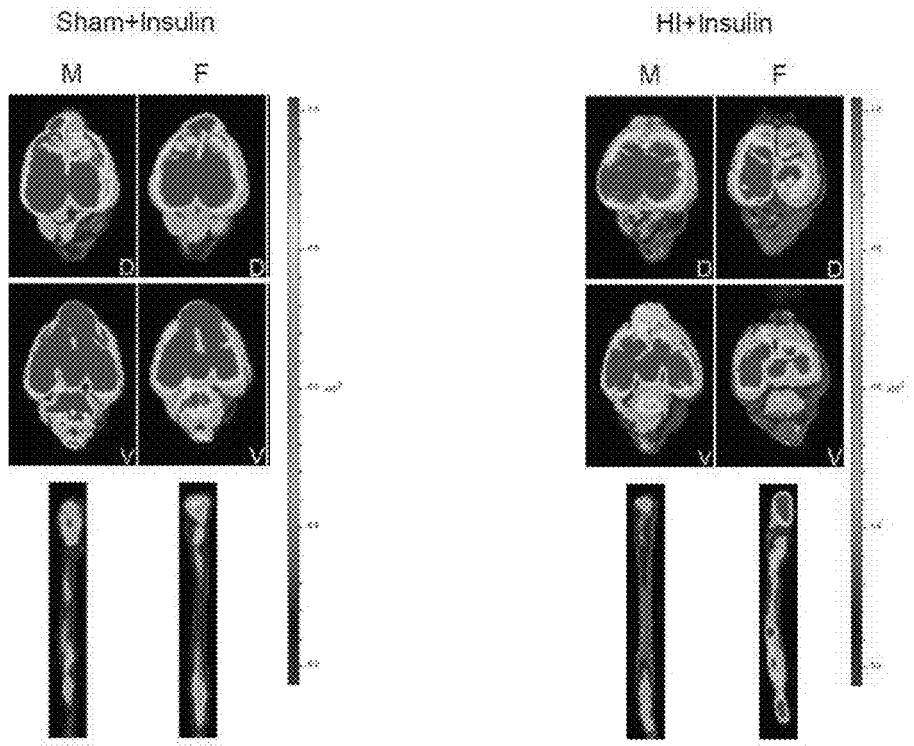

FIG. 1B illustrates a graph of blood glucose levels from pups at P11 provided InInsulin treatment following HI or Sham at P10.

FIGS. 2A-2D illustrate ex vivo imaging of dorsal (D, top raw) and ventral (V, middle raw) views of the brain and spinal cord (lower raw) using live imaging devices at 15 minutes after intranasal administration of Alexa 546-labeled insulin or vehicle following prior HI or Sham at P10. Blue color indicated no to very low concentrations while red color suggested the highest insulin concentration; M=male, F=female pups.

Figure 3A:
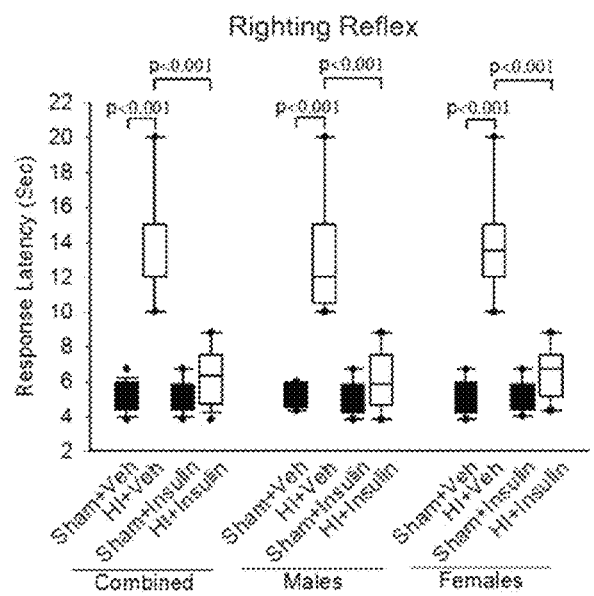
Figure 3B:
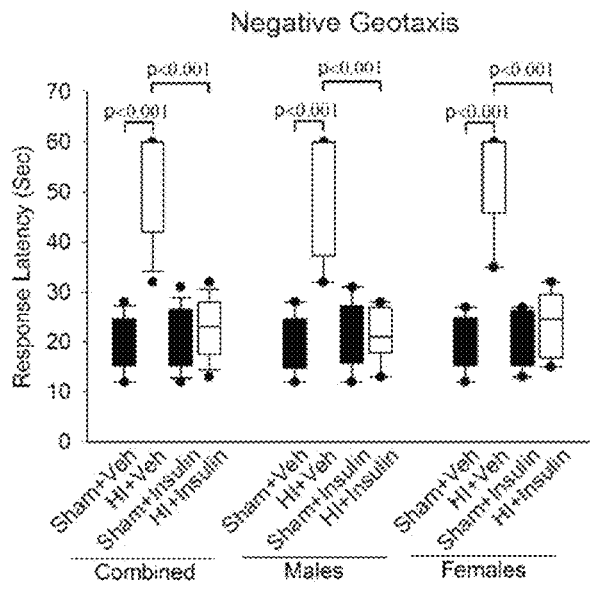
Figure 3C:
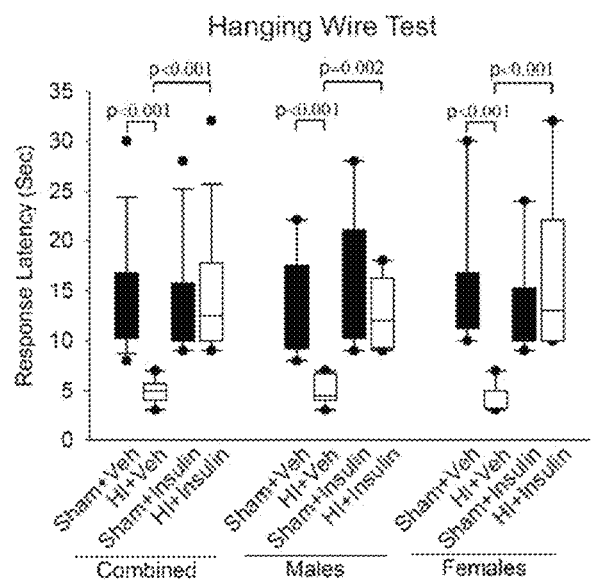
Figure 3D:
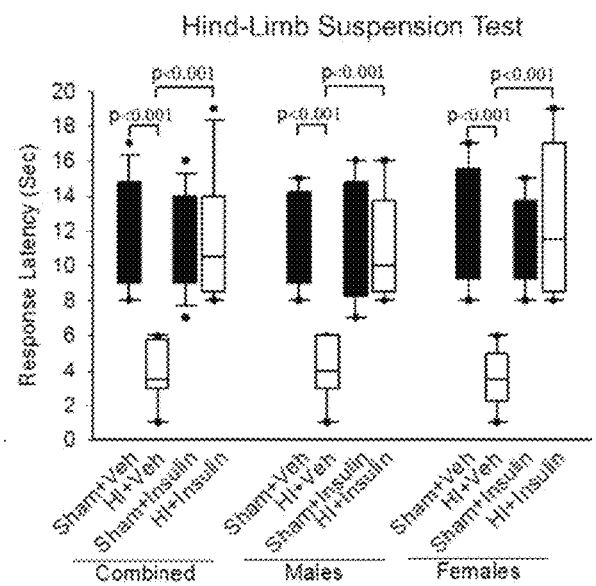

FIGS. 3A-3D are graphs illustrating the motor outcome of HI induced P10 neonates after InInsulin treatment at P11. FIG. 3A is a graph illustrating the results of righting reflex, FIG. 3B is a graph illustrating the results of negative geotaxis, FIG. 3C is a graph illustrating the results of the hanging wire test, and FIG. 3D is a graph illustrating the results of the hind-limb suspension test.

FIGS. 4A-4T illustrate representative photomicrographs of Nissl staining evaluating brain damage at P11 following HI or Sham and immediate InInsulin or Veh treatment at P10. FIGS. 4A-4D are photomicrographs of coronal brain sections at the bregma; FIGS. 4E-4H are photomicrographs illustrating dorsal hippocampal levels. Representative images of cortex (FIG. 4I-4L), hippocampus (FIG. 4M-4P) and striatum (FIG. 4Q-4T) are provided.

Figure 4U:
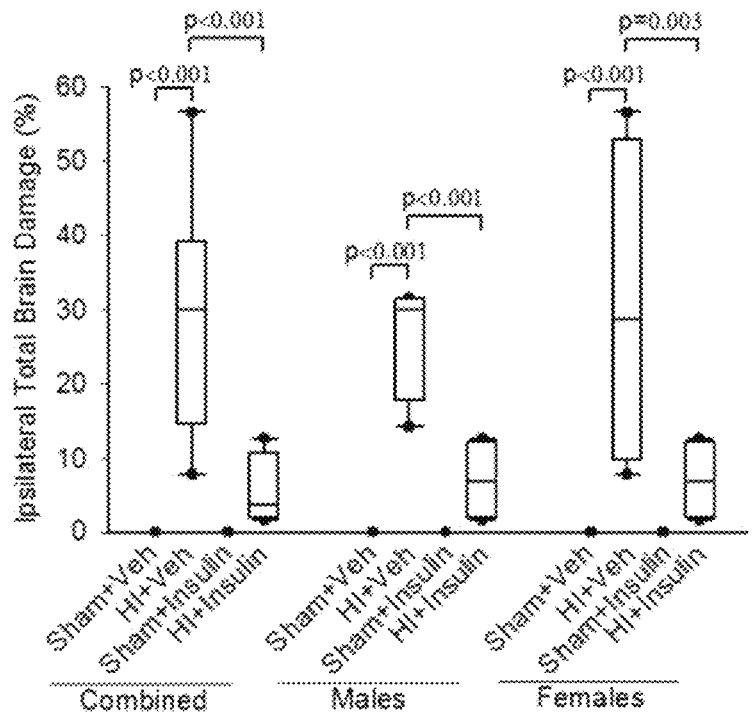
Figure 4V:
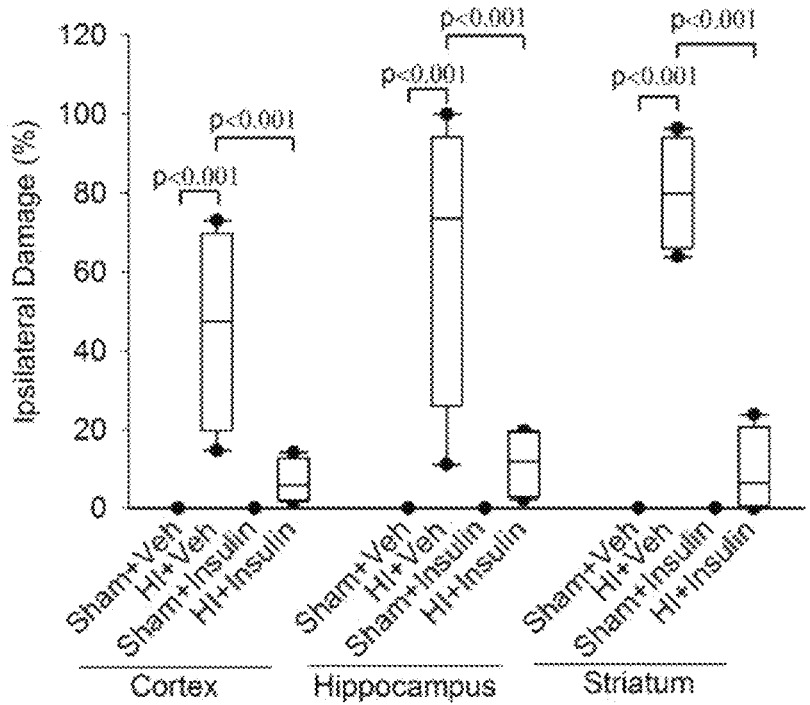

FIG. 4U and FIG. 4V are graphs illustrating stereology quantification of brain damage of ipsilateral hemisphere and different brain regions, respectively.

Figure 5A:
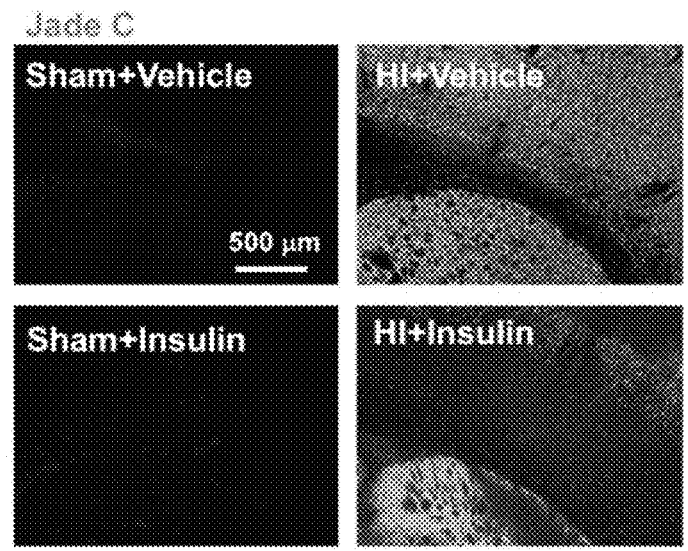

FIG. 5A includes representative photomicrographs of Jade C staining at P11 following HI or Sham and immediate InInsulin or Veh treatment at P10.

Figure 5B:
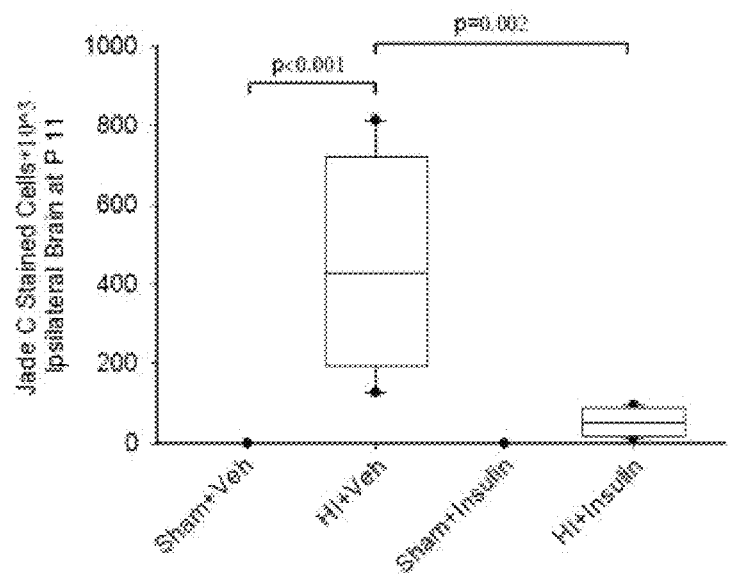

FIG. 5B shows a quantification of the Jace C stained cells of FIG. 5A.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview of HI

Brain injury following HI is an evolving process that is initiated during the insult and extends into a recovery period, the "reperfusion phase," which is amenable to potential intervention. Since the energy metabolism of the brain is independent of insulin whereas insulin receptors are expressed by neural cells, it has been proposed that insulin might play as yet unknown physiological roles in the central nervous system. Recent animal and clinical studies suggest that insulin could function as a neuroprotective agent through the PI3K pathway (also known as protein kinase B, a serine/threonine protein kinase), its resulting activation of phosphorylated AKT (p-AKT). In addition, insulin modulates higher brain functions including cognition and appetite. Intranasal insulin (InInsulin) could enhance long term declarative memory in healthy human volunteers, as well as improving the verbal memory in Alzheimer's patients. The neuroprotective property of InInsulin has not been investigated in an in vivo model of HI.

A growing body of evidence in rodent model and human studies supports the intranasal route for direct nose-to-brain delivery of the drugs for various neurological disorders bypassing the blood-brain barrier altogether. In human studies, insulin is detectable in the cerebrospinal fluid within 30 minutes after nasal application, suggesting that intranasal application may be a practical means to deliver insulin into the brain parenchyma.

The newborn rat model of HI is a well-established, reproducible model and has been used routinely for pre-clinical studies by us and others. However, P7 rat pups (7-day post-natal pups) have been traditionally used because the findings on P7 rat brains are more closely extrapolated to an immature (32-36-weeks gestational age) human infant than a full-term infant. In contrast, less work has used P10, which more closely aligned to full-term infant in neurological and brain development. The mortality and severity of damage vary depending on the duration of hypoxia and strain of rats. In the prior work, 140 min of hypoxic exposure of 7-day-old SD rat pups results in low mortality but moderate to severe brain damage. A variety of measures such as the pup's body temperature as well as a consistent interval (2-4 h) between arterial ligation and hypoxic exposure are required to minimize variability in the severity of brain damage in rat pups exposed to the same duration of HI exposure. The inventors of the present disclosure have found that 90 min of hypoxic exposure can more accurately mimic clinically relevant mild to moderate brain injury in control pups subjected to HI.

As provided by the present disclosure, insulin has been demonstrated to act as a neuroprotective agent in full term neonates using intranasal administration (i.e., InInsulin) providing neuroprotection against short-term adverse outcomes following neonatal HI.

Exemplary Treatment Methods

Embodiments of the present disclosure enable various methods for treating or reducing a likelihood of HI-induced brain damage and neurobehavioral dysfunction in neonates. An exemplary method includes intranasally administering, in need thereof (e.g., having been diagnosed with HIE or being suspected as having experienced an HI insult), an effective dose of InInsulin. The effective dose of InInsulin can be between 350 U to 2000 U insulin and can be calculated at, for example, from 75 U to 700 U insulin per kilogram of the neonate. It should be appreciated that in some embodiments, insulin is provided intranasally to neonates in a concentration ranging from 500 µg/kg to 10 mg/kg neonate weight, where half of the unit dosage form is delivered to each naris. The treatment methods disclosed herein can preferably and beneficially reduce or prevent brain damage without causing systemic hypoglycemia. Additionally, the disclosed treatment methods can be provided in a temporal range, such as within one or more days between delivery and 28 days post-delivery of the neonate.

In one embodiment, a method for the administration of InInsulin to a human neonate that is at least 36 weeks of gestational age at birth to reduce or prevent brain damage due to HIE after delivery. The delivery can be a traumatic delivery or be associated with an event that provides the attending healthcare provider (e.g., obstetrician or pediatrician) with a reasonable basis for suspecting the neonate to have experienced an HI insult. The method can include administering 175 U to 1000 U, or 600 U to 700 U, insulin to each nare of the neonate via an intranasal spray. Administration of said intranasal spray can reduce or prevent brain damage within the subject neonate without causing systemic hypoglycemia and can be administered within 1 hour or up to 1 day following the diagnosis or suspicion of HIE/HI insult. In some embodiments, the intranasal administration of insulin is provided one or more days between delivery and up to 28 days post-delivery of the neonate.

A method for treating or reducing a likelihood of hypoxia-ischemia induced brain damage and neurobehavioral dysfunction in neonates can include the act of identifying a neonate having experienced, or who is suspected as having experienced, a hypoxic-ischemic event, intranasally administering 175 U to 1000 U, or 600 U to 700 U, insulin to each nare of the neonate, and thereby reducing a likelihood of hypoxia-ischemia induced brain damage and neurobehavioral dysfunction in the neonate.

Treatment methods of the present disclosure additionally include receiving, at a neonate via intranasal administration, 175 U to 1000 U, or 600 U to 700 U, insulin to each nare without causing systemic hypoglycemia and thereby reduce a likelihood of HI-induced brain damage and neurobehavioral dysfunction.

The treatment methods disclosed herein can allow for the administered InInsulin to be received (and act) within deep regions of the brain and spinal cord. The regions of brain may include one or more areas that may include the right and left cerebellum, right substantia nigra, ventral temporal and occipital cortex, hippocampus, striatum and frontal cortex right substantia nigra, ventral temporal and occipital cortex, hippocampus, striatum, frontal cortex right olfactory bulb, ventral parietal cortex, hippocampus, substantia nigra, left olfactory bulb of the brain. In some embodiments, the intranasal delivery of insulin to the spinal cord was not delivered via the blood stream.

Embodiments of the present disclosure can be beneficially associated with the reduction or prevention of brain damage continuing for 2 or more weeks after the administration of InInsulin.

Pharmaceutical Compositions

As described herein, it is preferable to formulate the InInsulin as pharmaceutical compositions (e.g., formulations). As such, in yet another aspect, pharmaceutical compositions useful in the methods and uses of the disclosed embodiments are provided. A pharmaceutical composition is any composition that may be administered in vitro or in vivo or both to a subject to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate, preferably a neonate mammal. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible liquid formulation that is suitable for intranasal administration or contact (e.g., in vitro cell culture or ex vivo tissue applications). A formulation is compatible in that it does not destroy activity of an active ingredient therein (e.g., insulin) or induce adverse side effects that outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon intranasal routes of administration and dosage form. The pharmaceutical compositions should generally be formulated to achieve a physiologically compatible pH and may range from a pH of about 3 to a pH of about 11, preferably about pH 3 to about pH 7, depending on the formulation and route of administration. In alternative embodiments, it may be preferred that the pH is adjusted to a range from about pH 5 to about pH 8. More particularly, the pharmaceutical compositions may comprise a therapeutically or prophylactically effective amount of insulin, together with one or more pharmaceutically acceptable excipients. In yet other embodiments, the pharmaceutical compositions may be provided as a lyophilized powder where the final solution is insulin suspended in an aqueous saline solution. Optionally, the pharmaceutical compositions may comprise a combination of the compounds described herein or may include a second active ingredient useful in the treatment or prevention of HIE.

A pharmaceutical composition may also be formulated as a lyophilized solid that is reconstituted with a physiologically compatible solvent prior to intranasal administration.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences, incorporated herein by reference).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol, and ethanol; wetting or emulsifying agents; pH buffering substances; and the like. Liposomes are also included within the definition of pharmaceutically acceptable excipients.

The pharmaceutical compositions described herein may be formulated in any form suitable for intranasal administration. Compositions intended for intranasal use may be prepared according to any method known to the art for the manufacture of pharmaceutical compositions.

The pharmaceutical composition may be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

In one embodiment, the compounds described herein may be formulated for intranasal administration in a lipid-based formulation suitable for low solubility compounds. Lipid-based formulations can generally enhance the oral bioavailability of such compounds.

As such, in some embodiments, a therapeutically or prophylactically effective amount of a compound described herein can be combined together with at least one pharmaceutically acceptable excipient selected from the group consisting of medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve the intended therapeutic effect.

Dosages

The pharmaceutical compositions may, for convenience, be prepared or provided as a unit dosage form. Preparation techniques include bringing into association the active ingredient (e.g., insulin) and pharmaceutical carrier(s) and/or excipient(s). In general, pharmaceutical compositions are prepared by uniformly and intimately associating the active ingredient with liquid carriers or finely divided solid carriers or both. For example, an intranasal spray may be made by formulating the desired concentration of insulin within an aqueous solution (e.g, saline). The suspended formulation can then be distributed into discrete unit dosage forms.

Compounds (e.g., insulin), including pharmaceutical compositions can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (e.g., excipient, diluent, or vehicle) which, when administered is calculated to produce a desired effect (e.g., prophylactic or therapeutic effect or benefit). Unit dosage forms can contain a therapeutically relevant dose or unit, or an appropriate fraction thereof (e.g., half for administration to each nare of the neonate), of insulin. Preferably, a unit dosage form includes, for example, ampules or vials that may include a composition in a freeze-dried or lyophilized state or suspended within a sterile liquid carrier added prior to administration. To avoid overdosing or intradermal, subcutaneous, intravenous, or any other parenteral route of administration, unit dosage forms of InInsulin are included in single dose vials (single puff vials per nare or two puff vials, one puff per nare) in a device that will not be able to connect to any needle for intradermal, subcutaneous, intravenous, or any other parenteral route. In a preferred embodiment, therefore, the InInsulin unit dosage forms are not included in multi-dose kits or containers. Instead, pharmaceutical formulations are preferably packaged in single unit dosage forms for ease of administration and uniformity of dosage.

For intranasal delivery, the ideal volume in an adult human is 50-200 µL. For neonates/infants, the ideal volume is assumed to be about 50 µL or between 25-100 µL. To achieve the desired concentration of InInsulin within the foregoing volumes, it should be appreciated that intranasal compositions can be formulated between 2,500-40,000 U/mL, between about 5,000-20,000 U/mL, 10,000-15,000 U/mL, 12,000-14,000 U/mL, or any concentration selected within the foregoing ranges.

Compounds (e.g., insulin) can be administered in accordance with the methods at the prescribed frequency, typically once as a single bolus (delivered to a single nare or divided between each nare) within 10 days of HI insult. For example, InInsulin can be administered to the neonate substantially contemporaneously with, or within about 1-60 minutes or hours of the onset of a symptom, diagnosis of HI, or suspected HI (by an attending healthcare provider). For example, in an embodiment, a pharmaceutical composition contains an amount of a compound as described herein that is selected for administration to a patient within 1 hour to at most 1 day following HI insult or suspected HI insult.

The dosage may range broadly and may be based and calculated upon the per unit weight of the patient, as understood by those of skill in the art. Doses may vary depending upon simultaneous or subsequent treatments, general health, age, gender, or race of the subject, bioavailability, potential adverse systemic, regional, or local side effects, the presence of other disorders or diseases in the subject, and other factors that will be appreciated by the skilled artisan (e.g., medical or familial history). Dose amount, frequency, or duration may be increased or reduced, as indicated by the clinical outcome desired, status of the symptom(s) or pathology, and any adverse side effects of the treatment or therapy. The skilled artisan will appreciate the factors that may influence the dosage, frequency, and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to obtain the desired effect.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-24 hrs, includes 1, 2, 3, 4, 5, 6, 7 hrs, etc., as well as 1, 2, 3, 4, 5, 6, 7 minutes, etc., and so forth. Reference to a range or series of ranges, such as 1000-2000 U, 1200-1400 U, includes 1100-1900 U and 900-2100 U, in addition to 1000-1200 U, 1000-1400 U, 1200-2000 U, 1400-2000 U, etc.

Exemplary Treatment Systems

The present disclosure additionally extends to and enables systems for treating or reducing a likelihood of hypoxia-ischemia induced brain damage and neurobehavioral dysfunction in neonates. An exemplary system can include (i) a single dose vial comprising between 350 U to 2000 U intranasal insulin in a suspension within a solution (an aqueous solution, saline, or as otherwise described herein) and (ii) an intranasal delivery device operably connected to the single dose vial. The intranasal deliver device can be sized and shaped to prevent accidental administration of a by intradermal, subcutaneous, or intravenous routes of administration. In one embodiment, the intranasal delivery device is operable to deliver the single dose as two intranasal puffs, each intranasal puff comprising about half of the 350 U to 2000 U intranasal insulin and being delivered to a different nare of the same neonate. In some embodiments, the single dose vial comprises between 12,000 U/mL-14,000 U/mL intranasal insulin suspended within about 100 μL of the solution. It should be appreciated that the unit form dosage or applicable puff of intranasal medicament per nare can be at any concentration and/or as determined above.

CONCLUSION

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

EXAMPLES

The following examples as set forth herein are intended for illustrative purposes only and are not intended to limit the scope of the disclosure in any way.

Example 1. Neonate Survival Rates, Weights and Blood Glucose after Hypoxic-Ischemic Surgery To investigate whether InInsulin mitigates short-term microscopic changes of brain injury and neuro-behavioral outcomes following HI in newborn rats, a 10-day old rat model of HI-induced by the method of Levine with modification by Rice et al. and Patel et al was used. Additional measurement were performed to determine any sex-specific effects of HI and InInsulin.

Gestational timed pregnant Sprague-Dawley rats were housed in individual cages in the UMMC animal unit and maintained in accordance with the National Institutes of Health guidelines. Pups were allowed to deliver normally and day of birth was designated as P0. At P10, pups from each litter were divided by sex and assigned numbers. Pups were randomly divided into four groups: HI+Insulin; HI+Vehicle (Veh); Sham+Insulin; Sham+Veh. The male and female ratio was kept equal in each group. Each litter contributed at most 2 pups in any group.

On P10, rat pups were anesthetized with 3% isoflurane (Butler Animal Health Supply, Dublin, OH, USA). The right common carotid artery was exposed, isolated, and permanently doubly ligated. After surgery, the rat pups were returned to their dams for 2-3 h recovery. Hypoxic exposure was achieved by placing the rat pups in 1.5 L sealed jars immersed 5.5 cm deep in a 37° C. water bath and subjected to a warmed, humidified mixture of 8% oxygen/92% nitrogen bubbled through 37° C. water and delivered at 4 L/min. for 90 min duration. Pups were returned to their dams and allowed to recover and grow for follow up experiments.

In Sham exposure, P10 rat pups were anesthetized with 3% isoflurane (Butler Animal Health Supply, Dublin, OH, USA). The right common carotid artery was exposed, but not ligated. After surgery, the rat pups were returned to their dams for 2-3 h recovery. Pups were separated from dams and exposed to room air on a 37° C. pad for 90 min. After Pups were returned to their dams and allowed to recover and grow for follow up experiments.

For intranasal insulin or Vehicle administration, under light anesthesia with isoflurane, the pups were held in an upright position, and 25 μg of insulin (in 2.5 μl PBS) was applied to each naris using a 5 μl fine pipette tip. Each rat received a total of 50 μg insulin (1.44 units of insulin). Pups in Vehicle groups received the same amount of sterile PBS under light anesthesia. A dose of 50 μg of insulin was selected by extrapolating, based on average weight, the effective dose as derived by Pang et al. studying InInsulin's effects on 6-OHDA induced brain injury in juvenile rats.

A total of 64 pups underwent HI, and another 64 pups had Sham procedure, 32 of 64 pups following HI and 32 of 64 pups following Sham received InInsulin while the rest received saline. No mortality was noted in any of four groups.

Statistical analysis was performed with two-way ANOVA, with one factor being Sham/HI and the second Vehicle/Insulin, followed by Holm-Sidak testing for post-hoc analysis. Results are presented as mean±SEM and $p<0.05$ were considered to be significant. Based upon preliminary results, the number of animals required for clinical significance to find a difference of 30% between means were 8 males and 8 females, with the power of 85% and significance of $p<0.05$. All statistical analysis was performed using SigmaPlotVer 12.5.

Body weights of pups in all four groups at P10 before HI or Sham procedure and at P11 were measured. In FIG. 1A, rat pups were given InInsulin or Veh immediately following HI or Sham at P10. Body weight gain in grams measured at P11, n=8 pups/sex/group. The effect of Sham or HI depended upon whether pups received InInsulin or Veh, where there was a statistically significant interaction between Sham/HI and Insulin/Veh groups (two-way ANOVA, $F(1,63)=44.05$, $P<0.001$). On post-hoc analysis, compared to corresponding Sham groups, pups in HI+Veh (P<0.001) and HI+InInsulin (P<0.001) had a negative weight gain resulting in weight loss. Weight loss in HI+Veh was greater than HI+Insulin (P<0.001, n=16 pups/group).

In FIG. 1B, Blood glucose measured at different time points, n=16 pups/group. Two-way ANOVA followed by Post-hoc Holm-Sidak test. Compared to corresponding Sham groups, pups in HI+Veh and HI+Insulin had low blood glucose immediately following HI exposure but prior to Insulin or Veh administration (P<0.001, n=16 pups/group). At 30 minutes after Insulin or Veh administration, pups in HI+Veh (P=0.026) but not in HI+Insulin group had statistically higher blood glucose compared to the corresponding sham. No difference in blood glucose was noted between all groups at other time points measured. Sex had no effect or interaction with the effects of HI or Insulin on blood glucose at any time points measured (F $(1,63)$=0.678, P=0.414).

Example 2. Insulin Distribution in Brain Following Insulin Administration

To study the distribution of insulin in the brain following intranasal application, one set of pups was administered Alexa 546-labeled insulin (Nanocs Inc, Farmingdale, NY, USA). At 15 minutes after insulin-Alexa 546 (red color)/Vehicle administration, the pups were anesthetized with an overdose of isoflurane and their brains and spinal cords were surgically removed. The pups' brains and spinal cords were placed in the chamber for IVIS imaging (IVIS Spectrum imaging system, PerkinElmer, Johns Creek, GA, USA) ex vivo. Another set of animals were prepared for ELISA study. Right and left cerebellum, brain stem, hippocampi, and cerebral hemispheres were dissected on ice, separated from each other, snap frozen in dry ice, and stored at −80° C. for future processing and analysis. Total proteins were extracted using protein lysis buffer (Invitrogen). An ultrasensitive ELISA kit (ALPCO, Catalog #80-INSHUU-E0.1) was used to measure tissue insulin levels; the kit is specific for human but not rat insulin. A positive control, serum of diabetic patients, and rh-insulin (100 pg/mL) were included in each ELISA kit as controls. Normal rat brain tissue from corresponding brain regions was run in each ELISA to determine the baseline.

Ex vivo whole brain and spinal cord imaging using live imaging devices (IVIS Spectrum imaging system) was performed to provide an accurate picture of the overall bio-distribution of fluorescent labeling insulin. In FIG. 2, ex vivo images of dorsal (D, top raw) and ventral (V, middle raw) view of brain and spinal cord (lower raw) using live imaging devices at 15 minutes after intranasal administration of Alexa 546-labeled Insulin or Vehicle following prior HI or Sham at P10. Blue color indicated no to very low concentrations while red color suggested the highest insulin concentration; M=male, F=female pups. The results showed that Alexa 546-labeled insulin delivered to the central nervous system at 15 minutes after intranasal administration. Compared to Veh, both male and female pups showed higher insulin on ventral and dorsal view of brain in Sham+Insulin and HI+Insulin groups, although images of female pups in HI+Insulin suggested relatively higher insulin in spinal cord and lower insulin in brains. To accurately assess bio-distribution of intranasal insulin, all tissues of interest were analyzed by ELISA.

The specificity of ELISA kit for rh-insulin was first validated based on positive controls of serum of diabetic patients and rh-insulin. The calculated concentration of two positive controls in each ELISA consistently reached within 5% range of predicted values. The concentration of rh-insulin from the serum of pups from all four group were below the detectable limit; therefore, they were assigned a value of 0. The concentration of rh-insulin in different brain regions in pups from all group are shown in FIG. 2 at 15 mins after Intranasal Insulin or Veh administration following HI or Sham exposure.

In comparison to the corresponding Veh group, both male and female pups in Sham+Insulin and HI+Insulin had a significantly higher rh-insulin level in all brain regions on both sides of the brain (P<0.001, n=4 pups/sex/group). In comparison to corresponding Sham, very high level of rh-insulin was noted in the cervical and thoracic-lumbar spinal cord in both male and female pups in HI+Insulin group (P<0.001, n=4 pups/sex/group). In contrast to the corresponding Sham, right and left cerebellum of both sexes in HI+Insulin had a lower level of rh-insulin (P<0.05, n=4 pups/sex/group). In comparison to corresponding Sham, right substantia nigra, ventral temporal and occipital cortex, hippocampus, striatum, and frontal cortex in female pups in HI+Insulin had a lower level (P<0.05, n=4 pups/sex/group). Male pups compared to female pups, HI+Insulin had higher insulin in the right olfactory bulb, ventral parietal cortex, hippocampus, substantia nigra, left olfactory bulb and thoracic-lumbar spine (P<0.05, n=4 pups/sex/group).

Rh-insulin ELISA and fluorescence tracing results demonstrated that intranasal route is an effective delivering human insulin to the brain in this model of neonatal HI. This result is similar as described by Fan et al., which demonstrates the comparable distribution of insulin after intranasal administration in adult male SD rats. Contrary to findings in the adult rat, a substantial concentration of insulin in the cortex is achieved in neonatal rats. The distribution of insulin in various brain regions is not directly related to that region's physical distance from the olfactory bulbs. There is a significant amount of detectable insulin in the spinal cord; however, there was no detectable insulin in the rat's serum suggesting that the spinal cord delivery of insulin was not a result of blood-borne travel. At this time, the mechanism of the intra-parenchymal insulin travel and distribution in the various brain regions is uncertain. Because olfactory and trigeminal nerves are considered responsible for the nose to brain drug transport because both innervate the nasal cavities. At the cellular level, it is proposed that either intracellular via axons of nerves or extracellular via interstitial fluid mechanism are involved.

TABLE 1

Recombinant human insulin concentration (pg/mg of tissue) in brain regions.

| Source | Sham + Veh M | Sham + Veh F | HI + Veh M | HI + Veh F | Sham + Insulin M | Sham + Insulin F | HI + Insulin M | HI + Insulin F |
|---|---|---|---|---|---|---|---|---|
| Rt OB | 0.4 ± 1.1 | 0.1 ± 1.6 | 0.2 ± 2.3 | 0.2 ± 1.6 | 45 ± 13* | 38 ± 7.7* | 47 ± 15*§ | 16 ± 3.3* |
| Lt OB | 1.1 ± 1.2 | 0.6 ± 0.9 | 1.2 ± 1.0 | 0.9 ± 1.2 | 44 ± 11* | 36 ± 6.0* | 56 ± 17*§ | 23 ± 3.7* |

TABLE 1-continued

Recombinant human insulin concentration (pg/mg of tissue) in brain regions.

| Source | Sham + Veh M | Sham + Veh F | HI + Veh M | HI + Veh F | Sham + Insulin M | Sham + Insulin F | HI + Insulin M | HI + Insulin F |
|---|---|---|---|---|---|---|---|---|
| Rt FC | 0.0 ± 1.6 | 0.7 ± 0.6 | 1.7 ± 1.8 | 1.8 ± 0.9 | 17 ± 7.6* | 17 ± 4.9* | 12 ± 3.2*ζ | 7.4 ± 2.4* |
| Lt FC | 0.3 ± 1.7 | 0.4 ± 1.5 | 0.6 ± 1.9 | 1.5 ± 1.0 | 16 ± 3.4* | 19 ± 9.1* | 16 ± 9.3* | 18 ± 5.6* |
| Rt ST | 1.4 ± 0.9 | 0.3 ± 0.5 | 0.8 ± 1.5 | 1.8 ± 0.9 | 16 ± 3.8* | 17 ± 3.6* | 14 ± 4.7*ζ | 8.5 ± 1.1* |
| Lt ST | 1.3 ± 0.6 | 0.9 ± 0.9 | 0.2 ± 2.0 | 1.5 ± 1.0 | 16 ± 3.2* | 18 ± 5.5* | 16 ± 8.8* | 17 ± 7.5* |
| Rt Th | 0.6 ± 1.8 | 1.5 ± 1.2 | 1.0 ± 1.7 | 0.5 ± 0.6 | 10 ± 4.3* | 8.6 ± 4.4* | 7.3 ± 2.8* | 6.4 ± 2.3* |
| Lt Th | 0.9 ± 1.4 | 0.4 ± 0.7 | 1.9 ± 0.8 | 0.1 ± 1.8 | 9.4 ± 4.1* | 9.5 ± 5.1* | 7.5 ± 2.1* | 6.5 ± 1.9* |
| Rt dPCtx | 0.5 ± 2.1 | 0.8 ± 1.1 | 1.1 ± 1.4 | 0.4 ± 1.9 | 6.5 ± 2.0* | 6.4 ± 0.9* | 8.1 ± 5.0* | 6.9 ± 2.4* |
| Lt dPCtx | 1.1 ± 1.2 | 1.3 ± 0.8 | 0.8 ± 1.5 | 1.1 ± 1.1 | 6.4 ± 1.2* | 7.4 ± 2.2* | 7.3 ± 2.5* | 6.9 ± 1.7* |
| Rt vPCtx | 0.9 ± 2.2 | 0.8 ± 1.2 | 0.1 ± 2.0 | 1.1 ± 1.6 | 17 ± 7.2* | 16 ± 4.5* | 18 ± 5.6*§ | 8.0 ± 2.4* |
| Lt vPCtx | 1.6 ± 0.9 | 0.5 ± 1.2 | 0.5 ± 2.1 | 0.2 ± 1.4 | 16 ± 6.2* | 15 ± 4.1* | 14 ± 1.9* | 13 ± 2.9* |
| Rt HP | 1.1 ± 1.6 | 0.8 ± 1.4 | 0.9 ± 0.7 | 0.9 ± 1.2 | 16 ± 3.4* | 18 ± 3.9* | 17 ± 5.9*§ζ | 8.3 ± 2.1* |
| Lt HP | 0.2 ± 2.1 | 1.0 ± 0.9 | 1.5 ± 1.2 | 1.3 ± 0.8 | 17 ± 5.7* | 17 ± 4.3* | 22 ± 8.9* | 14 ± 3.9* |
| Rt HT | 1.1 ± 2.0 | 1.5 ± 1.7 | 0.4 ± 1.6 | 0.8 ± 0.9 | 9.2 ± 4.3* | 14 ± 6.8* | 9.1 ± 4.6* | 8.8 ± 3.9* |
| Lt HT | 1.2 ± 1.8 | 1.2 ± 1.8 | 1.7 ± 0.6 | 0.5 ± 1.8 | 8.3 ± 3.7* | 11 ± 4.3* | 10 ± 2.4* | 7.9 ± 4.6* |
| Rt dTC | 0.7 ± 2.4 | 1.2 ± 0.6 | 0.9 ± 1.4 | 0.3 ± 1.8 | 7.5 ± 2.7* | 6.8 ± 2.7* | 6.4 ± 2.4* | 6.7 ± 2.6* |
| Lt dTC | 1.2 ± 1.2 | 0.5 ± 0.9 | 0.9 ± 2.1 | 0.1 ± 1.5 | 8.7 ± 3.8* | 7.9 ± 2.2* | 8.3 ± 2.4* | 6.4 ± 2.9* |
| Rt vTC | 1.7 ± 0.9 | 1.1 ± 1.5 | 1.9 ± 0.6 | 0.7 ± 1.6 | 22 ± 10* | 22 ± 7.5* | 16 ± 5.8* | 8.4 ± 1.7*ζ |
| Lt vTC | 1.4 ± 1.1 | 1.2 ± 1.4 | 1.0 ± 1.0 | 1.0 ± 0.4 | 23 ± 10* | 23 ± 13* | 24. ± 10* | 15 ± 3.2* |
| Rt MB | 0.3 ± 2.5 | 1.0 ± 1.2 | 1.7 ± 0.8 | 0.7 ± 0.7 | 10 ± 2.7* | 9.8 ± 3.4* | 12 ± 4.9* | 9.2 ± 3.7* |
| Lt MB | 1.6 ± 1.3 | 0.9 ± 1.0 | 1.3 ± 1.1 | 1.7 ± 1.1 | 10 ± 4.0* | 13 ± 4.5* | 11 ± 4.4* | 10 ± 3.1* |
| Rt SN | 0.7 ± 2.2 | 0.7 ± 1.8 | 0.6 ± 1.5 | 0.2 ± 2.3 | 31 ± 7.6* | 32 ± 4.0* | 29 ± 9.8*§ | 11 ± 3.2*ζ |
| Lt SN | 1.2 ± 2.4 | 0.7 ± 0.4 | 1.3 ± 0.8 | 0.8 ± 1.3 | 30 ± 6.3* | 34 ± 7.0* | 33 ± 14.5* | 28 ± 9.9* |
| Rt CB | 0.6 ± 1.7 | 0.5 ± 1.2 | 0.2 ± 1.5 | 0 ± 1.4 | 22 ± 6.7* | 22 ± 10* | 11 ± 1.9*ζ | 10 ± 3.0*ζ |
| Lt CB | 0.8 ± 1.0 | 1.1 ± 1.1 | 0.5 ± 2.1 | 0.7 ± 1.4 | 21 ± 4.9* | 22 ± 10* | 10 ± 3.3*ζ | 11 ± 3.0*ζ |
| Rt Pons | 1.5 ± 0.6 | 1.2 ± 1.0 | 0.5 ± 1.5 | 0.1 ± 1.9 | 22 ± 12* | 17 ± 5.9* | 22 ± 9.1* | 21 ± 11* |
| Lt Pons | 1.0 ± 2.4 | 0.9 ± 0.9 | 1.2 ± 0.9 | 0 ± 1.7 | 22 ± 9.1* | 22 ± 10* | 29 ± 10* | 17 ± 5.0* |
| SP C | 1.2 ± 1.8 | 0.2 ± 1.9 | 1.0 ± 2.8 | 0.3 ± 2.3 | 36 ± 5.5* | 28 ± 13* | 47 ± 6.5*ζ | 85 ± 24*ζ |
| SPL | 0.1 ± 2.9 | 0.2 ± 1.5 | 0.8 ± 0.8 | 0.2 ± 1.2 | 10 ± 3.5* | 13 ± 3.9* | 21 ± 3.3*§ζ | 116 ± 16*ζ |

Data represent mean ± SD,
*P < 0.001 compared to corresponding Veh group,
§P < 0.05, compared to corresponding female group,
ζP < 0.05, compared to corresponding Sham group,
Three Way ANOVA followed by Post-hoc Holm-Sidak test,
n = 4 pups/sex/group.
M: male, F: female, Rt: right, Lt: left, OB: Olfactory bulb, FC: frontal cortex, ST: striatum, Th: thalamus, dPCtx: dorsal parietal cortex, vPCtx: ventral parietal cortex, HP: hippocampus, HT: hypothalamus, dTC: dorsal temporal and occipital cortex, vTC: ventral temporal and occipital cortex, MB: midbrain, SN: substantia nigra, CB: cerebellum, SP C: cervical spine, SPL: thoracic and lumbar spine.

Of further importance for this method of insulin delivery using intranasal administration, HI causes hypoglycemia but intranasal insulin treatment does not cause systemic hypoglycemia. At 30 min after InInsulin administration, pups do not have statically higher blood sugar compared to corresponding Sham. These results parallel various studies in humans which all demonstrate that intranasal insulin does not induce systemic hypoglycemia

Example 3. Neuro-Behavior Evaluation of HI Induced P11 Neonates after InInsulin Administration On P11, pup's neurobehavioral status was tested by an investigator blind to the group assignment using many commonly used neurobehavioral tests with modifications to assess for neurobehavioral injury. All animals were tested in the same order. Righting reflex, negative geotaxis, wire hanging maneuver, and hind-limb suspension tests were performed as indicators of neurological function at the early developmental stage.

A panel of neurobehavioral testing was performed on P11 in FIGS. 3A-3D. FIG. 3A is a graph illustrating the results of righting reflex, FIG. 3B is a graph illustrating the results of negative geotaxis, FIG. 3C is a graph illustrating the results of the hanging wire test, and FIG. 3D is a graph illustrating the results of the hind-limb suspension test. Suspension tests were performed at P11 to evaluate motor outcome following HI/Sham and immediate InInsulin/Veh treatment at P10. Two-way ANOVA followed by Post-hoc Holm-Sidak test, n=8 pups/sex/group.

In the righting reflex test in FIG. 3A, the effect of Sham/HI depended on whether pups received InInsulin or Vehicle, there was a statistically significant interaction between Sham/HI and Insulin/Veh (two-way ANOVA, F (1,63)=58.90, P<0.001). On post-hoc analysis, pups in HI+Veh took statistically significantly longer time to turn over compared to Sham+Veh (P<0.001, n=16 pups/group). Compared to HI+Veh, pups in HI+Insulin took much a shorter time to turn over (P<0.001). There was no statistically significant difference between Sham+Insulin and HI+Insulin group. In addition, sex had no interaction with the effects of HI/Sham or Insulin/Veh (three-way ANOVA, F (1,63)=0.035, P=0.851). When examined separately, both male and female pups had similar findings in all groups.

As shown in FIG. 3B, the negative geotaxis test of Sham or HI depended on whether pups received InInsulin or Veh, where there was a statistically significant interaction between Sham or HI and Insulin or Veh (two-way ANOVA, F (1,63)=71.27, P<0.001). On post-hoc analysis, pups in HI+Veh took a statistically significant longer time to turn and move up the incline compared to Sham+Veh (P<0.001, n=16 pups/group). In comparison to HI+Veh, pups in HI+Insulin took a much shorter time (P<0.001). There was no statistically significant difference between Sham+Insulin and HI+Insulin groups, and sex was not factor in the effects of HI/Sham or Insulin/Veh groups (three-way ANOVA, F (1,63)=0.028, P=0.868). When examined separately, all same sexed pups had similar findings as the analysis of the combined pups.

As shown in FIG. 3C, using the hanging wire test the effect of Sham/HI depended on whether pups received InInsulin or Veh, there was a statistically significant interaction between Sham/HI and Insulin/Veh groups (two-way ANOVA, F (1,63)=15.61, P<0.001). On post-hoc analysis, response latency in pups in HI+Veh was statistically significant shorter compared to Sham+Veh groups (P<0.001, n=16 pups/group). In comparison to HI+Veh, pups in HI+Insulin had a longer response latency (P<0.001). There was no statistically significant difference between Sham and HI Insulin treated group. Sex had no interaction with the effects of HI or Sham and Insulin or Veh group (three-way ANOVA, F (1,63)=2.204, P=0.143). When examined separately, both male and female pups had similar findings as of all pups.

As shown in FIG. 3D, using hind-limb suspension test the effect of Sham/HI depended on whether pups received InInsulin or Veh, there was a statistically significant interaction between Sham/HI and Insulin/Veh (two-way ANOVA, F (1,63)=33.77, P<0.001). On post-hoc analysis, response latency in pups in HI+Veh was statistically significant shorter compared to Sham+Veh (P<0.001, n=16 pups/group). In comparison to HI+Veh, pups in HI+Insulin had a longer response latency (P<0.001). There was no statistically significant difference between Insulin treated groups. Sex had no interaction on the effect of HI or Sham and Insulin or Veh (three-way ANOVA, F (1,63)=1.338, P=0.252). When examined separately, both male and female pups had similar findings as of all pups These demonstrated that InInsulin prevents the HI-induced poor performance in neurobehavioral testing in both sexes of term neonates. Other investigators have examined early neuro-behavior outcomes following neonatal HI; however these studies were early term neonates, P7. Rat pups following 120 minutes of HI at P7 took longer time in righting reflex and negative geotaxis as early as day 8. Abnormality in righting reflex lasted throughout the observation period of P8-P20. Pups performed better in geotaxis test at P20. Intraperitoneal injection of erythropoietin improves but not completely reverses the HI induced abnormality in righting reflex, negative geotaxis, and Hanging-Wire tests at P8 following HI at P7, although the duration of hypoxia was 120 minutes compared to 90 minutes used in this model.

Example 4. Effect of InInsulin on Brain Tissue Damage in HI Induced P11 Neonates The evaluation of brain Injury by Nissl Staining at 24 hours after the HI, at P11. Rat pups were anesthetized with an overdose of isoflurane and sacrificed by transcardiac perfusion with normal saline followed by 4% paraformaldehyde. The event of brain injury was estimated based on the results of Nissl staining of every sixth section of brain tissue. Nissl staining is a process by which Cresyl violet stain binds to RNA mainly located in the endoplasmic reticulum and nucleus of cells. The cross-sectional area of brain damage was measured for each mounted section. Brain damage was noted as a decreased in the density of tissue when magnified or significant change in parenchymal architecture when compared to the contralateral side. Brain damage volume was estimated by stereology method. Multiplying the cross-sectional area of damage by the thickness of each brain section and these volumes were added for all section to estimate the total brain damage volume.

Nissl staining of coronal sections of the brain at bregma and dorsal hippocampal level are shown in FIG. 4A-4H. Representative photomicrographs of Nissl staining evaluating brain damage at P11 following HI or Sham and immediate InInsulin or Veh treatment at P10. Coronal brain sections at the bregma (FIG. 4A-4D) and dorsal hippocampal (FIG. 4E-4H) levels shows obvious ipsilateral brain damage in HI+Veh groups. Scale bar=1 mm. Representative images of cortex (FIG. 4I-4L), hippocampus (FIG. 4M-4P) and striatum (FIG. 4Q-4T) in higher power shows disruption of brain architecture in exposed pups predominantly in HI+Veh, Scale bar=100 μm. FIG. 4U and FIG. 4V illustrate stereology quantification of brain damage of ipsilateral hemisphere and different brain regions, respectively. Two-way ANOVA followed by Post-hoc Holm-Sidak test, n=3-5 pups/sex/group.

In FIGS. 4A-4H, Nissl staining is shown from representative pups in all 4 groups at the level of the bregma (FIG. A-D) and hippocampus (FIGS. 4E-4H). Nissl staining showed significant damage to ipsilateral hemisphere causing tissue loss in coronal sections of brains from pups in HI+Veh group. Brains from pups in HI+Insulin had minimal focal damage scattered on the ipsilateral side. While no brain damage was visible in both Sham groups and left hemisphere in all groups.

High power magnification in all four groups are demonstrated in the cortex (FIGS. 4I-L), hippocampus (FIGS. 4M-4P), and striatum (FIGS. 4Q-4T). Pups from HI+Veh had disruption of architecture with a reduction in number and size of cells. Pups from HI+Insulin showed minimal abnormality while both Sham groups showed no abnormality.

Stereology quantification of total damage in the ipsilateral side showed that the effect of Sham or HI depended upon whether pups received InInsulin or Veh, where there was a statistically significant interaction between Sham/HI and Insulin/Veh (two-way ANOVA, F (1,29)=12.66, P<0.001). On post-hoc analysis, there was no brain damage noted in the sham groups, but pups in HI+Veh had on average 28% total ipsilateral brain damage compared to Sham+Veh group (P<0.001, n=6-8 pups/group). In comparison to HI+Veh groups, pups in HI+Insulin had much less damage, on average 6% (P<0.001). There was no statistically significant difference between Sham+Insulin and HI+Insulin group. Further, sex had no impact on the effects of HI or Sham and Insulin or Veh groups (three-way ANOVA, F (1,29)=0.202, P=0.657). When examined separately, both male and female pups had similar findings as of all pups.

Stereology quantification of regional damage of cortex (two-way ANOVA, F (1,29)=10.84, P=0.005), hippocampus (F (1,29)=9.507, P=0.008) and striatum (F (1,29)=76.27, P<0.001) on the ipsilateral side showed that the effect of Sham or HI depended upon whether pups received insulin. InInsulin or Vehicle groups, there was a statistically significant interaction between Sham or HI and Insulin or Veh. On post-hoc analysis, there was no damage noted in the sham groups, but pups in HI+Veh had on average 45.6% cortical damage, 64.6% hippocampal damage and 79.9% striatal damage on ipsilateral side compared to Sham+Veh (P<0.001, n=4-6 pups/group). Compared to HI+Veh, pups in HI+Insulin had much less damage, on average 6.9% cortical damage, 11.4% hippocampal damage and 9.2% striatal damage (P<0.001). There was no statistically significant difference between Sham+Insulin and HI+Insulin groups.

Example 5. Immunohistochemical Evaluation of Brain Injury in HI Induced P11 Neonates after InInsulin Administration Twenty-four hours after the HI (P11), rat pups were anesthetized with an overdose of isoflurane and sacrificed by transcardiac perfusion with normal saline followed by 4% paraformaldehyde. The brain injury was estimated based on the results of Fluoro-Jade C (Millipore, Billerica, MA, USA), a marker of degenerating neurons, staining in consecutive frozen coronary sections at a thickness of 40 μm prepared from the P11 rat brain. Fluoro-Jade C is a polyanionic fluorescein derivative that is sensitive and specifically binds to degenerating neurons. Brain sections were incubated with 1% NaOH/80% ethanol followed by 0.06% potassium permanganate for 5 and 15 minutes, respectively, to block the background staining, and then with 0.002% Fluoro-Jade C for 30 min before air-drying in the dark.

Three sections at each of two levels (bregma and middle dorsal hippocampal levels) of positively stained cells were examined by an observer blind to the group assignment. For each section, three randomly captured digital microscopic images were taken using Stereology System (MBF Bioscience, Williston, VT, USA) at the areas where the positive cells were abundant (mainly the cortex, striatum, or hippocampal area) in the ipsilateral hemisphere, and three randomly captured digital microscopic images will also be taken using Stereology System from the corresponding areas in the contralateral hemisphere. The number of positively stained cells in the three images from each area were averaged. The difference in each area, as well as the combined areas, was detected.

Representative photomicrographs are shown in FIG. 5A of Jade C staining at P11 following HI or Sham and immediate InInsulin or Veh treatment at P10. Immunohistochemistry using Jade C staining identifying degenerating cells (green) in cortex at hippocampal level of pups in all four groups. Extensive Jade C+cells are seen in the HI+Veh group compared to Sham+Veh. In contrast, fewer Jade C+cells were present in the HI+Insulin. Jade C+cells counted under fluorescent microscopy from three sections at each of bregma and middle dorsal hippocampal levels of ipsilateral hemisphere using Stereology system. Box and whiskers plot of the estimated number of positively stained is shown. Two-way ANOVA followed by Post-hoc Holm-Sidak test, n=4 pups/group.

In the representative micrographs shown in FIG. 5A, quantified in FIG. 5B, there was a lack of positively Fluoro-Jade C stained cells in both Sham groups. In contrast, positive staining was noted in both HI groups. Further, there is a qualitatively decreased staining in the HI+Insulin micrographs than compared to that in HI+Veh group. Quantification of estimated Fluoro-Jade C positive cells on the ipsilateral side showed that the effect of Sham/HI depended upon whether pups received. InInsulin or Vehicle neonates, there was a statistically significant interaction between Sham or HI and Insulin or Veh (two-way ANOVA, F (1,15)=7.73, P=0.017). In post-hoc analysis, there were no Fluoro-Jade C positive cells noted in the sham groups, however pups in HI+Veh had significantly high Fluoro-Jade C positive cells on compared to Sham+Veh groups (P<0.001, n=4 pups/group). Compared to HI+Veh, pups in HI+Insulin treated pups had significantly fewer cells (P=0.002). There was no statistically significant difference between Sham+Insulin and HI+Insulin group InInsulin prevents the HI-induced ipsilateral brain damage as measured by Nissl and Fluoro-Jade C. Both male and female pups have similar ipsilateral brain damage as of all pups. There are regional differences in HI-induced regional volume loss, striatum being the most vulnerable to HI than the hippocampus than the cortex. InInsulin protects striatum, hippocampus, and cortex equally. This is the first report to evaluate InInsulin its neuroprotective potency in an in vivo HI brain injury model. In a neonatal pig model of HI, LeBlanc et al. used IV regular porcine insulin to prevent hyperglycemia during glucose infusion before HI injury. Piglet in the insulin group fared slightly better, but the effect was likely secondary to blood glucose level than the direct effect of Insulin in brain. Change et al. has examined the effect of fasting hypoglycemia vs. insulin-induced hypoglycemia compared to normoglycemia in a neonatal piglet model of HI. Authors had achieved insulin-induced moderate hypoglycemia by a bolus injection of 1-2 μg/kg of regular insulin followed by continuous infusion of insulin in 0.9% normal saline. The flow rate of insulin was adjusted periodically to maintain the desired blood glucose level of 30-40 mg/dl. Insulin infusion was continued during HI exposure. Fasting hypoglycemia or insulin-induced hypoglycemia was not able to ameliorate brain injury. Lower brain glucose concentration was observed in the insulin-induced moderately hypoglycemic group and fasting mildly hypoglycemic group. Authors caution that insulin-induced moderate hypoglycemia might increase the risk of substrate deficiency and potential subsequent energy depletion during HI brain injury. The route, timing, and dose of insulin in our study are entirely different than the previous two studies discussed thus explain the difference in outcomes.

What is claimed is:

1. A method for treating or reducing a likelihood of hypoxia-ischemia induced brain damage and neurobehavioral dysfunction in neonates, comprising intranasally administering, to a neonate in need thereof, an effective dose of insulin comprising between 350 U to 2000 U insulin.

2. The method of claim 1, wherein the effective dose of insulin is calculated at between 75 U to 700 U insulin per kilogram of the neonate.

3. The method of claim 1, wherein intranasally administering the effective dose of insulin comprises intranasally delivering half of the effective dose to each nare of the neonate.

4. The method of claim 1, wherein the effective dose comprises 1200-1400 U insulin, the effective dose being delivered intranasally at 600 U to 700 U insulin to each nare of the neonate.

5. The method of claim 1, wherein the neonate is at least 36 weeks of gestational age at birth.

6. The method of claim 1, wherein the method further comprises identifying the neonate as having experienced, or who is suspected as having experienced, a hypoxic-ischemic event.

7. The method of claim 6, wherein the experienced or suspected hypoxic-ischemic event occurs at delivery or post-delivery.

8. The method of claim 1, wherein the intranasal administration is provided to the neonate at one or more days between delivery and 28 days post-delivery of the neonate.

9. The method of claim 6, wherein the intranasal administration is provided to the neonate only one time, the intranasal administration being provided within 1 hour to 1 day after the neonate experiences or is suspected of the hypoxic-ischemic event.

10. The method of claim 1, wherein the intranasal administration is provided to the neonate in the form of a nasal spray.

11. The method of claim 1, wherein intranasal administration comprises administering 25 µL to 150 µL of the nasal spray to each nare of the neonate.

12. The method of claim 11, wherein intranasal administration comprises administering the nasal spray to each nare of the neonate at a concentration between 10,000 U/mL and 15,000 U/mL.

13. The method of claim 1, wherein the intranasal administration is provided to the neonate without causing systemic hypoglycemia.

14. A method for treating or reducing a likelihood of hypoxia-ischemia induced brain damage and neurobehavioral dysfunction in neonates, comprising:
   identifying a neonate having experienced, or who is suspected as having experienced, a hypoxic-ischemic event;
   intranasally administering between 175 U and 1000 U insulin to each nare of the neonate without causing systemic hypoglycemia; and
   reducing a likelihood of hypoxia-ischemia induced brain damage and neurobehavioral dysfunction in the neonate.

15. The method of claim 14, wherein the neonate is at least 36 weeks of gestational age at birth.

16. The method of claim 14, wherein intranasal administration comprises administering 25 µL to 150 µL of a nasal spray to each nare of the neonate at a concentration of 10,000 U/mL to 15,000 U/mL.

17. A system for treating or reducing a likelihood of hypoxia-ischemia induced brain damage and neurobehavioral dysfunction in neonates, comprising:
   a single dose vial comprising between 350 U and 2000 U intranasal insulin suspended within an aqueous saline solution; and
   an intranasal delivery device operably connected to the single dose vial, the intranasal delivery device being sized and shaped to prevent accidental administration of the aqueous saline solution by intradermal, subcutaneous, or intravenous routes of administration.

18. The system of claim 17, wherein the intranasal delivery device is operable to deliver the single dose as two intranasal puffs, each intranasal puff comprising about half of the 350 U to 2000 U intranasal insulin and being delivered to a different nare of a same neonate.

19. The system of claim 17, wherein the single dose vial comprises 50 µL to 150 µL of the aqueous saline solution.

20. The system of claim 17, wherein the insulin is included in the aqueous saline solution at 10,000 U/mL-15,000 U/mL.

* * * * *